(12) United States Patent
Chukwu

(10) Patent No.: US 7,407,678 B2
(45) Date of Patent: *Aug. 5, 2008

(54) METHOD FOR ENZYMATIC TREATMENT OF A VEGETABLE COMPOSITION

(75) Inventor: Uchenna N. Chukwu, Minnetonka, MN (US)

(73) Assignee: Chi's Research Corporation, Minnetonka, MN (US)

( * ) Notice: Subject to any disclaimer, the term of this patent is extended or adjusted under 35 U.S.C. 154(b) by 772 days.

This patent is subject to a terminal disclaimer.

(21) Appl. No.: 10/619,403

(22) Filed: Jul. 14, 2003

(65) Prior Publication Data

US 2004/0009262 A1    Jan. 15, 2004

Related U.S. Application Data

(63) Continuation-in-part of application No. 09/495,960, filed on Feb. 2, 2000, now abandoned, which is a continuation-in-part of application No. 09/196,844, filed on Nov. 20, 1998, now Pat. No. 6,033,692.

(51) Int. Cl.
*A23F 5/00*    (2006.01)

(52) U.S. Cl. ............................ 426/45; 426/52; 426/629

(58) Field of Classification Search .................. 426/44, 426/66, 52, 61, 629, 640, 45; 435/187, 209, 435/197, 201, 210, 212, 219 225
See application file for complete search history.

(56) References Cited

U.S. PATENT DOCUMENTS

| | | | |
|---|---|---|---|
| 2,965,490 A | 12/1960 | Rusoff | |
| 3,640,723 A * | 2/1972 | Uhlig et al. | 426/46 |
| 3,705,810 A * | 12/1972 | Lendvay | 426/45 |
| 3,845,220 A * | 10/1974 | Suzuki | 426/45 |
| 4,214,007 A | 7/1980 | Hase et al. | |
| 4,301,251 A | 11/1981 | Rumyantseva et al. | |
| 4,333,955 A | 6/1982 | Murata et al. | |
| 4,376,128 A | 3/1983 | Lunde | |
| 4,904,484 A | 2/1990 | Small et al. | |
| 5,037,662 A | 8/1991 | Poulose et al. | |
| 5,100,679 A | 3/1992 | Delrue | |
| 5,120,552 A * | 6/1992 | Sherman et al. | 426/50 |
| 5,298,265 A | 3/1994 | Poulose et al. | |
| 5,445,957 A | 8/1995 | Rohde, Jr. et al. | |
| 5,651,967 A | 7/1997 | Rohde, Jr. et al. | |
| 5,720,971 A | 2/1998 | Beauchemin et al. | |
| 5,888,562 A | 3/1999 | Hansen et al. | |
| 6,015,913 A | 1/2000 | Kealey et al. | |
| 6,194,020 B1 | 2/2001 | Myers et al. | |
| 6,399,139 B2 | 6/2002 | Myers et al. | |
| 6,555,147 B1 | 4/2003 | Xu | |

FOREIGN PATENT DOCUMENTS

| | | | |
|---|---|---|---|
| JP | 58-138347 | * | 8/1983 |
| WO | 95/22601 | * | 8/1995 |

* cited by examiner

*Primary Examiner*—Arthur L Corbin

(57) ABSTRACT

A method of processing a vegetable that includes providing a vegetable composition having a first outer layer to which an enzyme is applied for a time that is sufficient to form an enzyme-degraded vegetable. The enzyme-degraded vegetable is capable of absorbing components, such as water, additives or enzymes that further process the vegetable.

16 Claims, No Drawings

METHOD FOR ENZYMATIC TREATMENT OF A VEGETABLE COMPOSITION

CROSS-REFERENCE TO RELATED APPLICATION(S)

This application is a continuation-in-part of application Ser. No. 09/495,960, filed Feb. 2, 2000, now abandoned, which is a continuation-in-part of application Ser. No. 09/196,844, filed on Nov. 20, 1998, now U.S. Pat. No. 6,033,692.

BACKGROUND OF THE INVENTION

The present invention generally relates to using enzymes to process raw vegetables prior to human consumption. More specifically, the present invention relates to forming a enzyme-degraded vegetable product with improved processing and nutritional characteristics and to a method of making the vegetable product.

During the last several years, consumer interest in eating foods that are nutritionally balanced with an adequate source of protein, fat, carbohydrates, fiber, vitamins and minerals has increased. Growing concern over chronic diseases, such as cancer, diabetes and heart disease have motivated consumers to seek foods for consumption that are effective in treating chronic diseases while promoting a healthier lifestyle. As evidenced by the growing health foods market, whole foods market, and dietary supplements market, consumers believe that consumption of phytochemicals in their diet may contribute to a lower risk and a lower incidence of chronic diseases. As used herein, a "phytochemical" means a chemical substance produced by a plant with a demonstrated health benefit.

Consumption of vegetables having phytochemicals may pose several problems. The presence of anti-nutritional components such as indigestible sugars, enzyme inhibitors, nutrient-binding substances or toxic compounds typically render a vegetable containing the beneficial phytochemicals unfit for consumption. Low concentrations of the desired phytochemical in the vegetable is another problem for consumers, especially if the concentration of the phytochemical is considered too low to deliver a health benefit.

Heat or pressure processing of vegetables to eliminate anti-nutritional components in the vegetable prior to consumption is the traditional approach used by food manufacturers. However, heat and/or pressure processing may eliminate most, if not all phytochemical levels during the manufacturing process. In addition, the manufacturing process may require physical and/or chemical pre-treatment strategies, such as cooking, boiling, application of strong acids, and/or hydration of the raw vegetable prior to processing, in order to adequately process the vegetable. Unfortunately, physical and/or chemical pretreatment strategies of the vegetable prior to processing may include complicated steps that increase the overall costs associated with vegetable production.

BRIEF SUMMARY OF THE INVENTION

The present invention includes a method of processing vegetables prior to human consumption by applying enzyme(s) to a raw vegetable for a time that is sufficient to form an enzyme-degraded vegetable under normal atmospheric pressures followed by deactivation of the enzyme(s). The enzyme-degraded vegetable is further capable of absorbing other components such as water, additives or enzymes that further modify the raw vegetable.

DETAILED DESCRIPTION

The present invention includes a method of processing vegetables. In the method, an aqueous enzyme composition is applied to a raw vegetable composition under normal atmospheric pressure for a time that is effective to form an enzyme-degraded vegetable composition. After degrading, the enzyme-degraded vegetable composition can be processed by one or more additional processing steps that transforms the enzyme-degraded into a vegetable product destined for human consumption.

As disclosed in application Ser. No. 09/196,844, now U.S. Pat. No. 6,033,692 and application Ser. No. 09/495,960, now abandoned, which are incorporated herein by reference, enzymes can be used to hydrate dry edible beans so that subsequent processing of these hydrated edible beans by canning or the like is more easily accomplished without having to use excessive temperatures and/or pressures. Traditional vegetable processing techniques often require the use of high temperatures and/or high pressure during the manufacturing process due in part to the presence of a tough outer layer on vegetables that functions as a barrier. Such high temperatures and/or pressures increase the cost and complexity of processing vegetables. In addition, such high temperatures and/or high pressures may ultimately reduce the nutritional quality of processed vegetables by lowering phytochemical levels in a manner that reduces consumer acceptability and consumption.

The present invention includes enzymatic degradation of raw vegetables under normal atmospheric pressures prior to (1) human consumption or (2) the use of more traditional processing techniques that involve high pressures and/or temperatures to complete production. Additionally, the present invention represents a novel approach that helps to reduce the need for high temperatures and/or pressures during vegetable processing. In addition, since enzymatic processing of vegetables in accordance with the present invention typically occurs under normal atmospheric pressure, specialized equipment is typically not required and subsequent reduction in the cost and complexity of manufacturing vegetables may be realized. Furthermore, enzymatic degradation of vegetables prior to using more traditional processing techniques may also permit a reduction in time, energy and/or other resources that are required to complete processing of raw vegetables.

While not wanting to be bound to theory, it is believed that when one or more enzyme(s) that are capable of degrading one or more target substrates in a first outer layer of a raw vegetable composition, are applied to the first outer layer of the raw vegetable composition in accordance with the present invention, the enzyme(s) degrade the target substrates of the first outer layer of the raw vegetable composition to form an enzyme-degraded vegetable composition having a compromised first outer layer. Consequently, the use of the aqueous enzyme composition is effective to degrade, tenderize, and/or the raw vegetable composition. In addition, the use of the aqueous enzyme composition to degrade the raw vegetable composition renders the raw vegetable composition more absorbent to water or other liquids and permits subsequent in situ modification of the raw vegetable composition by addition of ingredients like vitamins, minerals, other enzymes that catalyze specific reactions or the like.

As used herein, the term "enzyme" means any complex protein produced by a living cell that is capable of at least catalyzing a specific biochemical reaction on one or more target substrates. The term "enzyme" is also meant to encompass any complex protein capable of catalyzing a specific biochemical reaction that is substantially free of any microorganism. All references to enzyme is also understood as encompassing any synthetically- or genetically-produced identical copy of the enzyme that is identical in molecular structure to the enzyme that originated in a living organism.

As disclosed in U.S. Pat. No. 6,033,692 and application Ser. No. 09/495,950, the enzyme(s) that may be included as part of the aqueous enzyme composition maybe generally characterized as carbohydrase(s). As used herein, the term "carbohydrase" means any enzyme that is capable of at least catalyzing hydrolysis of a carbohydrate-containing target substrate. By "hydrolysis" is meant enzymatic degradation of the carbohydrate-containing target substrate that includes complex carbohydrates like cellulose, hemicellulose, pectin, xylan chains of hemicellulose, and/or polymers of other 5-carbon sugars into their sugar components like pentoses or hexoses.

Furthermore, the term "hydrolysis" is not meant to include the use of microorganisms that produce carbohydrases to hydrolyze and/or degrade raw vegetable compositions in accordance with the present invention. The application of microorganisms that produces carbohydrases and other enzymes to process raw vegetable compositions is commonly referred to as microbial fermentation. Additionally, although microbial fermentation may involve some degree of hydrolysis, microbial fermentation is known to further transform sugar components like pentoses or hexoses into organic acids that increases the acidity, reduces the pH, and alters the texture and taste of the fermented vegetable composition. In contrast, the present invention uses enzymes that are substantially free of microorganisms to hydrolyze, tenderize, and/or degrade the raw vegetable composition. Furthermore, use of the aqueous enzyme composition in accordance with the present invention typically results in a decrease in the acidity of, and/or increase in the pH of the aqueous enzyme composition after processing as disclosed in U.S. Pat. No. 6,033,692 and application Ser. No. 09/495.960.

Preferably, cellulase is one carbohydrase that is used as part of the aqueous enzyme composition. Still more preferably, cellulase that is substantially free of any microorganism is included as part of the aqueous enzyme composition. Most preferably, cellulase that is substantially free of any microorganism is used to degrade, hydrolyze and/or tenderize the raw vegetable composition when practicing the present invention. Cellulase may be derived from a number of different sources, such as fungal sources, plant sources, microbial sources, animal sources, or any combination of any of these.

Besides cellulase, it is believed that other carbohydrases, such as hemicellulase, alpha-galactosidase, invertase, mannanase, beta-gluconase, beta-glucanase, arabanase, polygalacturonase, ferulic acid esterase, xylanase, beta-galactosidase, beta-fructofuranosidase, alpha-amylase, beta-amylase, pectinase, pectin depolymerase, pectin methyl esterase, pectin lyase, glucoamylase, oligo-1,6 glucosidase, lactase, beta-d-glucosidase, or any combination of any of these are suitable additional non-exhaustive examples of carbohydrases that may be used separately or in combination with cellulase in accordance with the present invention.

Preferably, the aqueous enzyme composition includes cellulase and any combination of hemicellulase, alpha-galactosidase, mannanase, beta-gluconase, beta-glucanase, arabanase, polygalacturonase, xylanase, beta-galactosidase, beta-fructofuranosidase, alpha-amylase, beta-amylase, pectinase, invertase, pectin depolymerase, pectin methyl esterase, pectin lyase, glucoamylase, oligo-1,6 glucosidase, lactase, or beta-d-glucosidase to degrade the raw vegetable composition under normal atmospheric pressures, prior to (1) human consumption or (2) application of traditional processing techniques like cooking, pressure-cooking or the like.

More preferably, a blend of cellulase and hemicellulase is used in the present invention to degrade, tenderize and/or render the raw vegetable composition more absorbent to water, enzymes, additives or the like. Still more preferably, a blend of cellulase, hemicellulase and pectinase is used in the present invention to degrade the raw vegetable composition so that subsequent processing can be practiced with reduced temperature and/or pressure requirements.

A preferred example of an enzyme blend that may be used as part of the aqueous enzyme composition is Viscozyme®L, available from Novozymes of Franklinton, N.C. Alternate examples of enzymes that are suitable for use as part of the aqueous enzyme composition is Econase® CE, available from Enzyme Development Corporation of New York, N.Y., Cellulase 4000 or Crystalzyme Cran that is available from Valley Research Inc., of South Bend, Ind.

When enzymes are used during vegetable processing, enzymes may be applied in any form, such as a granular form, or a vapor form, or as part of the aqueous enzyme composition as noted above. The application form that is selected preferably permits the enzyme to (1) contact the vegetable composition being treated, and (2) remain in contact with the vegetable composition being treated for a time that is sufficient to degrade the target substrate. Preferably, the enzyme(s) is applied to the raw vegetable composition as part of the aqueous enzyme composition.

The aqueous enzyme composition may include one or more enzyme component(s), one or more optional catalyst component(s), one or more optional pH-modifying component(s), one or more optional additive(s) or one or more optional solvent component(s). The components of the aqueous enzyme composition may be supplied as individual components, or supplied in various prepared mixtures of two or more components, that are subsequently combined to form the aqueous enzyme composition.

The enzyme component(s) may include only the enzyme (s), the enzyme(s) and water, or may optionally include additional components. The enzyme component(s) may be supplied as individual components, or supplied in various prepared mixtures of two or more components, that are subsequently combined to form the enzyme component(s). Additionally, the enzyme component may be supplied in granular form, vapor form, or as part of an aqueous enzyme component.

The concentration of the enzyme(s) in the enzyme component may generally range from about 0.0001 weight percent to about 100 weight percent, based on the total weight of the enzyme component. The enzyme component may optionally include sucrose, fructose, ash, alcohol, and any other components that are compatible with, and do not interfere with the biochemical rate of catalysis of the enzyme.

Preferably, the concentration of the enzyme component is an amount that is effective to tenderize, hydrolyze, modify and/or degrade the raw vegetable composition. Still more preferably, the concentration of the enzyme component is an amount that is effective to degrade the first outer layer of a raw vegetable composition. Most preferably, the concentration of the enzyme component that is used in accordance with the present invention is an amount that is effective to degrade the first outer layer of a raw vegetable composition, tenderize, hydrolyze, modify and/or degrade the raw vegetable composition, and permit further modification of an inner portion of the raw vegetable composition.

Furthermore, it is to be understood that the concentration of the enzyme component(s) may vary depending on the amount of time that the enzymes remain in contact with the raw vegetable composition. Furthermore, if a short exposure time is employed, then higher concentrations of the enzyme component(s) would be required to achieve the desired degree of degradation, tenderization, hydrolysis and/or modification of the raw vegetable compositions. Similarly, if longer exposure times are employed, then the concentration of the enzyme component(s) would be reduced to arrive at the desired result.

As an example, when the enzyme component is supplied in the form of a liquid, the enzyme component can be applied at a concentration of less than about 10 weight percent, based on the total weight of the raw vegetable composition to permit water absorption by the raw vegetable compositions like dry edible beans. More preferably, when the enzyme component is supplied in the form of a liquid, the enzyme component is applied at a concentration of less than about 5 weight percent, based on the total weight of the raw vegetable composition to permit water absorption by raw vegetable compositions.

Similarly, when the enzyme component is supplied in the form of a granular powder, the enzymes can be applied at a concentration of less than about 5 weight percent, based on the total weight of the raw vegetable composition to tenderize, hydrolyze and/or enzymatically modify the raw vegetable composition. More preferably, when the enzyme component is supplied in the form of a granular powder, the enzyme component is applied at a concentration of less than about 1 weight percent, based on the total weight of the raw vegetable composition to tenderize, hydrolyze and/or enzymatically modify the raw vegetable compositions.

The aqueous enzyme composition may optionally include one or more catalyst component(s) in a form that is readily applied to the raw vegetable composition. A catalyst, when included as part of the aqueous enzyme composition, generally enhances the biochemical rate of catalysis of the enzyme component(s). Increasing the biochemical rate of catalysis of the enzyme component(s) may decrease the application time of the aqueous enzyme composition to the raw vegetable composition or the amount of the aqueous enzyme composition applied to the raw vegetable composition.

Alternatively, the catalyst component may be applied separately from the aqueous enzyme composition, either before, during, or after application of the aqueous enzyme composition to the raw vegetable composition. Additionally, the source(s) of the catalyst may be applied in particulate form, as part of an aqueous composition, or in a vapor form so long as the particular form selected results in application to and uptake by the vegetable composition. Some non-exhaustive examples of catalysts that may be included as part of the aqueous enzyme composition are salts that include calcium ions, copper ions, magnesium ions, iron ions, sodium ions, zinc ions, manganese ions, potassium ions, or any combination thereof. The catalyst component(s) may be supplied as individual components, or supplied in various prepared mixtures of two or more components, that are subsequently combined to form the catalyst component(s).

The aqueous enzyme composition may include one or more pH-modifying component(s) that are capable of adjusting the acidity, hereinafter referred to as the pH, of the aqueous enzyme composition. Furthermore, the pH of the aqueous enzyme composition will vary depending on the enzyme(s) present in the aqueous enzyme composition.

Preferably, the pH of the aqueous enzyme composition is about 2.0 to about 7.0. Still more preferably, the pH of the aqueous enzyme composition is about 3.0 to about 7.0 when degrading, tenderizing, hydrolyzing and/or enzymatically modifying the raw vegetable composition. In addition, extremely low pH values of less than about 1.0 are typically effective in deactivating the enzyme component(s) when practicing the present invention. Consequently, human consumption or addition of strong acids that reduce the pH of the aqueous enzyme composition are believed effective in deactivating the enzyme component(s) of the aqueous enzyme composition.

Some non-exhaustive examples of pH modifying substances include organic acids, such as acetic acid, tartaric acid, malic acid, succinic acid, citric acid, or the like; phosphoric acid; or buffering agents of such organic acids, such as sodium acetate, sodium malate, sodium succinate, sodium citrate, or the like. Basic compounds like sodium hydroxide or the like may be included as part of the pH-modifying substances that are suitable for use in the present invention.

Some non-exhaustive examples of optional additives that may be included as part of the aqueous enzyme composition include natural and/or artificial flavors; artificial colors; naturally-occurring pigments, such as, for example, chlorophyll, anthocyanin, betalain, betaine, carotenoid, anthoxanthins; herbs; spices; vitamins; minerals; plant extracts; essential oils; sugars such as sucrose, fructose, glucose, or maltose; preservatives; emulsifiers, such as mono-glycerides, distilled mono-glycerides, di-glycerides, distilled di-glycerides, or lecithin; any additive that improves the aqueous enzyme composition application to, uptake by, or subsequent processing of the vegetable composition; or any combination of any of these. The optional additives may be supplied as individual components, or supplied in various prepared mixtures of two or more components, that are subsequently combined to form the optional additives.

The aqueous enzyme composition may also include one or more solvent component(s). The solvent component(s) preferably facilitate homogenous blending of the enzyme component(s), the optional catalyst component(s), the optional pH-modifying component(s), the optional additives, or any combination thereof. The solvent component(s) preferably facilitate aqueous enzyme composition application to, and uptake by the vegetable composition. Some non-exhaustive examples of solvents that may be included in the aqueous enzyme composition include water; oils; alcohol, such as ethanol, methanol, propanol, butanol, or the like; hexane; or any combination thereof. The solvent component(s) may be supplied as individual components, or supplied in various prepared mixtures of two or more components, that are subsequently combined to form the solvent component(s).

Liquid water is the preferred solvent for the aqueous enzyme composition as water is typically required for enzymatic degradation, tenderization and/or hydrolysis. The amount of liquid water included as part of the aqueous enzyme composition depends on an initial concentration of water in the raw vegetable composition, the biochemical rate of catalysis, and/or the desired final product characteristics of the enzyme-degraded raw vegetable composition. Generally, the amount of the aqueous enzyme composition is such that the raw vegetable composition is completely contacted by the aqueous enzyme composition. As an example, when degrading raw edible beans, water is included as part of the aqueous enzyme composition at a range of about 2 to about 5 times the weight of raw edible beans. Similarly, when tenderizing raw greens like collads, kale, turnip, or mustard greens, water is included as part of the aqueous enzyme composition at a range of about 1 to about 2 times the weight of the raw greens.

An example of component concentration ranges for a preferred formulation of the aqueous enzyme composition is presented in Table 1 below:

TABLE 1

| COMPONENT | CONCENTRATION (weight percent)* |
|---|---|
| Enzyme component | about 0.0001 to about 99 |
| Catalyst component | 0 to about 25 |
| pH-modifying component | 0 to about 10 |
| Optional additives | 0 to about 50 |
| Solvent component | 0 to about 99 |

*based on the total weight of the aqueous enzyme composition

In general, any conventional blending apparatus and technique that is suitable for homogeneously blending the enzyme component(s), the optional catalyst component(s), the optional pH-modifying component(s), the optional additives, the optional solvent component(s), or any combination thereof, such as a mixer, may be used to form the aqueous enzyme composition.

As used herein, the term "application" means to apply the aqueous enzyme composition to the raw vegetable composition by spraying; knife-coating; spreading; printing; soaking; exposing; immersing; slop-coating; dip-coating; roller-coating; dipping; contacting; brush-coating; squirting; submerging; foam padding; leaf-sprinkling; sprinkling; pouring; slop-padding; or any combination thereof.

The temperature of the aqueous enzyme composition depends on the initial temperature of the vegetable composition, the temperature for the optimum biochemical rate of catalysis of the enzyme component(s), and/or the desired characteristics of the enzyme-degraded vegetable composition. The temperature of the aqueous enzyme composition is at the optimum temperature for a maximum biochemical rate of catalysis of the enzyme component(s) of the aqueous enzyme composition.

Generally, the temperature of the aqueous enzyme composition may range from about 30° F. to about 250° F. Preferably, the temperature of the aqueous enzyme composition ranges from about 30° F. to about 250° F. Still more preferably, the temperature of the enzyme composition ranges from about 40° F. to about 200° F. Most preferably, the temperature of the aqueous enzyme composition ranges from about 40° F. to about 195° F.

Although the aqueous enzyme composition maybe applied to the raw vegetable composition at a constant temperature, the temperature of the aqueous enzyme composition maybe increased at any time during application of the aqueous enzyme composition to the raw vegetable composition. Generally, increasing the temperature increases the biochemical rate of catalysis, and/or water absorption.

However, a negative impact on the texture of the raw vegetable composition may occur if the temperature of the aqueous enzyme composition is too high, such as more than about 250° F., or the temperature of the aqueous enzyme composition is changed too rapidly during application. Furthermore, too high temperatures may inactivate the enzyme component of the aqueous enzyme composition, therefore care is required to avoid premature inactivation of the enzyme component(s) before attaining the desired degree of hydrolysis, tenderization, degradation and/or enzymatic modification when practicing the present invention.

Steam can also be injected into the aqueous enzyme composition to during or after application of the aqueous enzyme composition to the raw vegetable composition to (1) optionally increase the temperature of the aqueous enzyme composition applied to the raw vegetable composition, (2) optionally increase the moisture content of the vegetable composition, (3) optionally gelatinize any starch granules of the vegetable composition, (3) optionally increase the efficacy of the biochemical rate of catalysis of the aqueous enzyme composition, or (3) optionally deactivate the enzyme component in the aqueous enzyme composition.

As noted, inactivation of the enzyme component(s) readily occurs at high temperatures, therefore, care is required to avoid premature inactivation of the enzyme component(s) prior to attaining the desired degree of degradation, tenderization and/or hydrolysis of the raw vegetable composition.

The aqueous enzyme composition is typically applied to the raw vegetable composition at normal atmospheric pressures. By "normal atmospheric pressures" is meant atmospheric pressures of about 14.7 psi. Furthermore, it is to be understood that "normal atmospheric pressures" also includes atmospheric pressures that occurs even under varying altitudes, temperatures, humidities, or the like.

Additionally, the term "normal atmospheric pressures" is not meant to include application of positive or negative pressures to the raw vegetable composition prior to or during application of the aqueous enzyme composition in a manner that facilitates degradation, tenderization, hydration and/or hydrolysis.

As used herein, the term "vegetable" means a plant-based food that originated as a living organism of the Plantae kingdom. All references to "vegetable" are to be understood as encompassing any genetically-altered copy of the plant that originated as a living organism of the Plantae kingdom. Furthermore, the term "vegetable" encompasses leaves, seeds, roots, tubers, bulbs, flowers, fruits, stems, shoots, nuts, or any combination of any of these that originated as a living organism of the Plantae kingdom.

The raw vegetable composition of the present invention typically contains a first outer layer that substantially covers, overlays, and/or is in adhesive contact with a second inner layer of the raw vegetable composition when practicing the present invention. When the first outer layer is in adhesive contact with the second inner layer, adhesive contact may be accomplished through bonding via cementing substances like pectic substances.

The first outer layer of the vegetable composition typically includes a fibrous network of cellulose; xylan chains of hemicellulose; hemicellulose; polysacccharides of five-carbon sugars; lignin; pectic substances, such as protopectin, pectic acid, pectin, or any combination thereof; vitamins; minerals; anti-nutritional components; or any combination of any of these. Some non-exhaustive examples of the first outer layer may include a seed coat of a legume or lentil; a bran layer of a grain; a stem wall of a vegetable; a skin of a root, tuber, and/or bulb vegetable; a peel of a fruit; a testa or a seed wall of a nut.

The second inner layer of the raw vegetable composition generally includes a network of starch granules, fat globules, fiber, proteins, vitamins, minerals, water, phytochemicals, anti-nutritional components, or any combination of any of these. In addition, all references to the second inner layer is also understood to encompass the inner portion of the raw vegetable composition and thus, the second inner layer may also include seeds embedded in the vegetable composition. Some non-exhaustive examples of anti-nutritional components of a vegetable composition include flatulence-causing sugars, such as, for example, raffinose, verbascose and stachyose; lectins; nutrient-binding substances, such as phytic acid; other indigestible polysaccharides; enzyme inhibitors, such as trypsin inhibitor; or toxic compounds, such as goitrogens, solanine, or oxalic acid.

Preferably, the first outer layer is connected or in adhesive contact to the second inner layer or inner portion of raw vegetable compositions when practicing the present invention. By "connected or in adhesive contact" is meant that the raw vegetable composition has a substantial portion of the first outer layer connected to the inner portion or second inner layer of the raw vegetable composition. Additionally, removal of the first outer layer of the raw vegetable composition by peeling, chemicals, grating for example is preferably avoided when practicing the present invention.

As used herein, the term "raw" refers to vegetable composition(s) that are uncooked, un-boiled, dry, edible, as being in a natural condition, not processed or any combination of any of these. Furthermore, it is to be understood that the term "raw" refers to the condition of the first outer layer, the second inner layer or both the first and second layers of the vegetable composition when practicing the present invention. For example, as disclosed in U.S. Pat. No. 6,033,692 raw dry edible beans contain an outer seed coat and inner cotyledon that have not been cooked or subjected to a boiling and/or cooking step prior to application of the aqueous enzyme composition. The aqueous enzyme composition is therefore applied to the raw edible beans in a manner that degrades the seed coat or first outer layer of the raw beans, and thereby promote rapid hydration of the raw beans.

In addition, the raw vegetable composition is preferably a whole raw vegetable compositions. By "whole" is meant that the raw vegetable composition has not been subjected to techniques like maceration, pulverization, grating, grinding or the like. For example, dry edible beans that have not been ground, grated, macerated or pulverized are examples of whole raw vegetable compositions. Similarly, green leafy vegetables such as collards, kale or the like that have not been ground, grated, macerated or pulverized are preferred examples of whole raw vegetables that may be used in accordance with the present invention.

Raw vegetable compositions that are in the form of a seed having less than about 40 weight percent moisture content, and preferably less than about 30 weight percent moisture content may be used in accordance with the present invention. Examples of seeds include raw beans, as noted above, which are the dry edible raw seeds from a plant of a Leguminosae family. A raw bean typically has about 12 to about 14 weight percent moisture content or less, although certain raw beans contain more than about 14 weight percent moisture content and are suitable for use as the raw vegetable composition of the present invention. Some non-exhaustive examples of raw beans include pinto beans, light red kidney beans, black-eye peas, lentils, mung beans, pinkie beans, great northern beans, green lima beans, yellow lima beans, garbanzo beans, carob beans, cacao beans, coffee beans, split and/or whole peas, peanuts, yellow peas, green peas, soybeans, black beans, vanilla bean, or any other edible seed from plants of the Leguminosae family.

In addition, preferred raw vegetable compositions for the present invention do not include raw vegetable compositions containing an additional outer layer on top of the first outer layer. Examples of an additional outer layer on top of the first outer layer includes grains that contain a waxy coat, such as waxy coats that include cutin or other wax- and/or lipid-containing molecules that cannot be hydrolyzed or degraded by carbohydrases such as cellulase, hemicellulase, pectinases and the like.

While preferred raw vegetable compositions include raw vegetable compositions that do not contain a waxy layer and a moisture content of less than about 30 weigh percent, certain raw vegetable compositions like bulgur have been found to undergo rapid hydration when an aqueous enzyme composition containing celluase and hemicellulase is used to soak bulgur.

Raw vegetable compositions that are generally in the form of a nut may also have less than about 40 weight percent moisture content and may also be included as part of the raw vegetable composition when practicing the present invention. As used herein, a "nut" means a hard shelled dry fruit or seed with a separable first outer layer that substantially encloses an interior kernel.

Some non-exhaustive examples of vegetable compositions in the form of a nut that may be used in accordance with the present invention include an acorn nut, an almond nut, a brazil nut, a butternut, a cashew nut, a chestnut, a coconut, a filbert nut, a hazelnut, a hickory nut, a macadamia nut, a pecan nut, a pine nut, a pistachio nut, a walnut, or any recognized edible nut from a recognized edible vegetable source.

It is also to be understood that the term "raw vegetable composition" is meant to encompass raw vegetable compositions that may have been washed with steam, hot, warm and/or cold water in an attempt to remove dirt and the like from the raw vegetable composition. Cleaning, washing or dirt removal from the vegetable composition may also include the application of food-grade detergents or chemicals using sprinkler-type equipment or soaking equipment. Such cleaning, washing or dirt removal techniques are believed to not significantly remove the first outer layer of the raw vegetable composition from the second inner layer or inner portions of the raw vegetable compositions, and therefore, use of such cleaning, washing or dirt removal techniques prior to application of the aqueous enzyme composition are permissible when practicing the present invention.

In addition, physical and/or chemical pretreatment strategies designed to initiate breakdown, improve the porosity of the first outer layer of raw vegetable compositions, remove certain cellulose and hemicellulose fractions or expose degradation sites have been practiced in the widespread belief that enzymatic degradation cannot proceed without such pre-treatment strategies. Physical pre-treatment strategies includes application of positive or negative pressure prior to application of the aqueous enzyme composition to vegetable compositions. Furthermore, chemical pre-treatment strategies include application of strong acid solutions, pre-soaking, boiling or cooking of vegetable compositions that typically increase the moisture content of vegetables prior to application of the aqueous enzyme composition.

The present invention avoids these complicated processing strategies by applying the aqueous enzyme composition to the raw vegetable composition under normal atmospheric pressures without having first subjected the raw vegetable composition to strong acidic solutions, pre-soaking, boiling or cooking prior to application of the aqueous enzyme composition. Such physical and/or chemical treatments are typically reserved, and preferably conducted after the aqueous enzyme composition has degraded the raw vegetable composition so that the enzyme component(s) are deactivated after attaining the desired degree of enzyme degradation.

It is also to be understood that the term "whole raw vegetable composition" is meant to encompass broken a raw vegetable composition that (1) has a first outer layer that is in adhesive contact with the second layer and (2) an exposed second inner layer or inner portion of the raw vegetable composition. For example, in the manufacture of refried beans, broken portions of whole beans still contain a seed coat and exposed cotyledons. Such broken portions of whole raw beans can be soaked or exposed to the aqueous enzyme composition of the present invention to degrade the seed coat and tenderize the cotyledons prior to human consumption or any subjecting the beans to any other remaining processing steps required for manufacturing refried beans.

Similarly, as disclosed in application Ser. No. 09/495,960, raw green leafy vegetables may be chopped prior to application of the aqueous enzyme composition to permit enzymatic degradation and subsequent tenderization of the raw green leafy vegetables. Chopping does not remove or diminish the fibrous network present in raw green leafy vegetables. Enzymatic treatment of raw green leafy vegetables facilitates a reduction in time and energy required to cook raw green leafy vegetables when compared to raw greens that have not been enzymatically degraded.

As noted above, the length of time the aqueous enzyme composition is applied to the raw vegetable composition typically depends on the raw vegetable composition, the desired degree of degradation, the concentration of the enzyme component(s) and/or the desired characteristics of the enzyme-degraded vegetable composition. The length of time used in practicing the present invention may range from about 1 second to more than about 24 hours. As examples, the length of time to degrade raw vegetable compositions having a moisture content of less than about 30 weight percent is about 1 second to about 2 hours while the length of time to tenderize raw vegetable compositions is about 1 second to about 2 hours as well.

While not wanting to be bound to theory, it is believed that application of the aqueous enzyme composition in accordance with the present invention transforms the first outer layer and/or the second inner layer or inner portion of the raw vegetable composition into a crater-like, mesh-like or sieve-like network of degraded sites. Additionally, the aqueous enzyme composition may generate holes throughout the first outer layer and/or the second inner layer of the vegetable composition that facilitates absorption of water, additives, or enzymes. The aqueous enzyme composition may also target a wide range of substrates within the raw vegetable composition, therefore, the breakdown of these substrates may occur and aid in the reduction of cook time of the enzyme-degraded raw vegetable composition.

Partial degradation of the first outer layer of the vegetable composition permits absorption of the enzyme component(s), the optional pH-modifying component(s), the optional additives, the optional solvent component(s), or any combination thereof, into the raw vegetable composition while the aqueous enzyme composition is still in contact with the first outer layer. Thus, absorption of the enzyme component(s), the optional pH-modifying component(s), the optional additives, the optional solvent component(s), or any combination thereof, into the raw vegetable composition may occur during or after application of the aqueous enzyme composition to the raw vegetable composition when practicing the present invention.

The rate at which the enzyme-degraded vegetable composition is capable of absorbing the enzyme component(s), the optional pH-modifying component(s), the optional additives, the optional solvent component(s), or any combination thereof, may be expressed as the absorbency of the raw vegetable composition. As used herein, the absorbency of the vegetable composition may be characterized in units of grams of the enzyme component, the optional pH-modifying component, the optional additive, or the optional solvent component per minute of application time. The specific absorbency of a raw vegetable composition is defined herein as the absorbency of an enzyme-degraded vegetable composition per gram of enzyme-degraded vegetable composition.

The benefits of the enzyme-degraded raw vegetable composition include an increase in the absorbency of the raw vegetable composition of a component, such as, for examples, water, additives, or other enzymes that may be used to further process the raw vegetable composition. In addition, processing the enzyme-degraded raw vegetable composition by conventional means, after enzymatic degradation, such as by freezing, hydrating, steaming, freeze-drying, canning, frying, boiling, drying, extrusion, cooking, baking, roasting, pulverizing, fermenting, enzyme, pasteurizing, extracting, milling, puffing, steam-pressure cooking, or any combination thereof, is improved since the first outer layer of the raw vegetable composition that typically functions as a barrier during conventional is degraded.

Once sufficient degradation of the raw vegetable composition has occurred to form the enzyme-degraded raw vegetable composition, the enzyme-degraded raw vegetable composition may be separated from the aqueous enzyme composition and further subjected to processing steps, such as, for example, blanching, that inactivates any enzyme component(s) remaining in the enzyme-degraded raw vegetable composition. Alternatively, transferring both the raw enzyme-degraded vegetable composition and the aqueous enzyme composition to equipment that permits further processing by freezing, hydrating, steaming, freeze-drying, canning, frying, boiling, drying, extrusion, cooking, baking, roasting, pulverizing, fermenting, enzyme, pasteurizing, extracting, milling, puffing, steam-pressure cooking, or any combination thereof, is also effective in deactivating any enzyme component(s) remaining in the enzyme-degraded raw vegetable composition and the aqueous enzyme composition.

The present invention is more particularly described in the following examples that are intended as illustrations only since numerous modifications and variations within the scope of the present invention will be apparent to those skilled in the art.

A Method of Improving the Absorbency of Raw Vegetable Compositions

A series of experiments were conducted using raw pinto beans as the raw vegetable composition to improve the absorbency of a raw vegetable composition using enzymes. Approximately 740 grams of water was added to an amount of vinegar and brought to any one of the temperature ranges specified in Table 2 below. About 12 to about 13 grams of Viscozyme®L, supplied by Novo Nordisk Biochem North America Inc., of Franklinton, N.C., was added to the water and vinegar mixture to form an aqueous enzyme composition with an initial pH of about 4.0. Viscozyme®L is a blend of cellulase, hemicellulase and pectinase enzymes. About 250 grams of raw pinto beans for each experiment conducted at any one of the temperature ranges were added to the aqueous enzyme composition and allowed to soak for about 60 minutes under normal atmospheric pressure. The raw pinto beans were then drained, and transferred to about 750 grams of water at about 200° F. for about a 5 minute blanch. The experiments were randomized and repeated twice to ensure reproducibility. A control batch of raw pinto beans were subjected to an aqueous composition that did not include enzymes. Furthermore, the control batch of raw pinto beans was allowed to soak for about 240 minutes. The results are presented below in Table 2:

TABLE 2

| VEGETABLE COMPOSITION | TEMP (° F.) | CONC. (% by weight) | ABSORB-ENCY* | SPECIFIC ABSORB-ENCY** |
|---|---|---|---|---|
| Pinto (1) | 50-60 | 5% | 0.93 | 0.00372 |
| Pinto (2) | 50-60 | 5% | 0.75 | 0.00300 |
| Pinto (1) | 110-120 | 5% | 3.21 | 0.01284 |
| Pinto (2) | 110-120 | 5% | 2.67 | 0.01068 |
| Pinto (1) | 150-160 | 5% | 3.18 | 0.01272 |
| Pinto (2) | 150-160 | 5% | 3.27 | 0.01308 |
| Pinto (control) | 150-160 | 0% | 1.17 | 0.00468 |

*grams of water per minute of soak time
**grams of water per minute of soak time per gram of bean Table 2 illustrates that incorporating a blend of cellulase, hemicellulase and pectinase as part of the aqueous enzyme composition that is subsequently applied to the first outer layer of a raw vegetable composition increases both the absorbency and the specific absorbency of a vegetable composition by a factor of about 3.

A Method of Degrading and/or Tenderizing Raw Vegetable Compositions

A series of experiments were conducted to degrade and/or tenderize raw vegetable compositions in the form of raw navy beans and raw leafy green vegetables. While raw navy beans typically have a moisture content of less than about 30 weight percent, raw green leafy vegetables have a moisture content of more than about 30 weight percent. It has been discovered that application of an aqueous enzyme composition to raw whole vegetable compositions having a moisture content of less than or more than about 30 weight percent is effective to degrade and/or tenderize the raw whole vegetable compositions. Tenderization of raw vegetable compositions results in a reduction in the cook and/or process time of raw vegetable compositions when compared to raw vegetable compositions that have not been subjected to enzymatic degradation.

Two hundred and fifty grams of raw navy beans were soaked for 60 minutes in aqueous enzyme compositions of varying concentrations. The temperature was maintained between 110° and 120° F. and the initial pH was about 4.00. Approximately 740 grams of water was added as part of the aqueous enzyme composition and vinegar was the pH-modifying component. The concentration of the granular enzyme (Celluase 4000) that was supplied by Valley Research, Inc., was about 0.15 weight percent of the raw navy beans. After soaking, the raw navy beans were blanched in the aqueous enzyme composition for 5 minutes at about 200° F. to form blanched beans. Next, the blanched beans were cooked for about 45 minutes until done. Control raw navy beans that were not soaked in an aqueous enzyme composition took more than about 2.5 hours to cook until done.

Similarly, about 250 grams of raw collards were sprayed with an aqueous enzyme composition that contained about 12-13 grams of Viscozyme, 740 grams of water and enough vinegar to reach an initial pH of about 4.0. In addition, the initial temperature of the aqueous enzyme composition was about 110° F. The raw collards were allowed to soak for about 60 minutes and then cooked in the aqueous enzyme composition. The raw greens cooked in about 45 minutes compared to the time of more than 2 hours that were required to cook raw greens not subjected to enzymatic treatment.

A Method of Enzymatically Processing a Raw Vegetable Composition

As noted, the aqueous enzyme composition may include one or more enzyme component(s). Furthermore, if an aqueous enzyme composition containing a first enzyme component and a second enzyme component are applied to a raw vegetable composition in accordance with the present invention, both the first or second enzyme components maybe used to enzymatically process the raw vegetable composition and form an enzyme-processed vegetable composition. Typically application of the aqueous enzyme composition that includes first and second enzyme components occur under normal atmospheric pressures and temperatures that can range from about 40° F. to about 250° F. and preferably from about 40° F. to about 195° F. In addition, the pH values range from about 2.0 to about 7.0.

More specifically, when the aqueous enzyme composition contains a first enzyme component that is designed to degrade the first outer layer of raw vegetable compositions, such as a first enzyme component that includes cellulase, hemicelullase and pectinase, the first enzyme component typically degrades the first outer layer of the raw vegetable composition to form an enzyme-degraded raw vegetable composition. Next, if the aqueous enzyme composition further includes a second enzyme component that is designed to degrade, and/or hydrolyze any target substrates located in the second inner layer or inner portion of the raw vegetable composition, the second enzyme component is able to penetrate the inner portion through the degraded sides of the enzyme-degraded raw vegetable composition and degrade the target substrates. The target substrate may be one or more anti-nutritional components in the second inner layer of the vegetable composition.

Alternatively, two or more separate aqueous enzyme compositions may be applied to the raw vegetable composition when practicing the present invention. For example, a first aqueous enzyme composition that includes cellulase and hemicellulase maybe applied to a raw vegetable composition having a moisture content of less than about 30 weight percent under normal atmospheric pressures and temperatures to form an enzyme-degraded raw vegetable composition. Next, a second aqueous enzyme composition that contains an enzyme component that is effective to degrade and/or hydrolyze target substrates either in the first outer layer or the second inner layer can be applied to the enzyme-degraded vegetable composition. The second aqueous enzyme composition is able to penetrate the enzyme-degraded vegetable composition and therefore, is capable of degrading and/or hydrolyzing desired target substrates in the enzyme-degraded vegetable composition.

It is believed that the compromised first outer layer of the enzyme-degraded raw vegetable composition allows the second enzyme component or the second aqueous enzyme composition to enter and degrade any anti-nutritional components in the enzyme-degraded raw vegetable composition. Additionally, water included as part of the aqueous enzyme composition(s) may also enter through the degraded first outer layer to hydrate the enzyme-degraded raw vegetable composition. If water is absorbed by the enzyme-degraded raw vegetable composition, the water in the enzyme-degraded raw vegetable composition may facilitate degradation of anti-nutritional components of the enzyme-degraded raw vegetable composition by the second enzyme component or the second aqueous enzyme composition.

After sufficient enzymatic degradation by the second enzyme component, or the second aqueous enzyme composition, an enzyme-processed raw vegetable composition is formed that can be further subjected to other processing steps, such as, for example, blanching, that inactivates any enzyme component(s) remaining in the enzyme-processed vegetable composition.

Preferably, the enzymes that are included as part of the first enzyme component include the above noted enzymes that are effective in degrading the first outer layer of raw vegetable compositions. The enzyme(s) that may be included as part of the second enzyme component or second aqueous enzyme composition are carbohydrases, proteases or any combination thereof. Any of the examples of carbohydrases as suitable for use during application of the first enzyme component may be used as part of the second enzyme component in any combination with the first enzyme component, for degradation of any anti-nutritional component of the raw vegetable composition in accordance with the present invention.

As used herein, the term "protease" means any enzyme that is capable of at least catalyzing degradation of a protein-containing target substrate. One particular form of a protease that may be used as part of the second enzyme component in accordance with the present invention is an endoprotease. As used herein, an "endoprotease" means any enzyme that is capable of degrading an internal peptide bond on a target substrate having one or more peptide bonds. Another particular form of a protease that may be used as part of the second enzyme component in accordance with the present invention is an "exoprotease". As used herein, an "exoprotease" means any enzyme that is capable degrading a peptide bond located at a terminal portion of a target substrate having one or more peptide bonds. Either the endoprotease or the exoprotease may be derived from a number of different sources, such as fungal sources, plant sources, microbial sources, animal sources, or any combination of any of these.

Besides the carbohydrases and proteases, it is believed that other enzymes, such as oxido-reductases that are capable of at least catalyzing oxidation-reduction reactions on target substrates, transferases that are capable of at least catalyzing the transfer of functional groups on target substrates, hydrolases that are capable of at least hydrolyzing bonds, such as ester bonds or acid anhydride bonds on target substrates, lyases that are capable of at least adding onto a double bond on target substrates, isomerases that are capable of at least isomerizing bonds on target substrates, or ligases that are capable of at least forming bonds on target substrates, or any combination of any of these, provide sufficient degradation, hydrolysis and/or enzymatic modification of any anti-nutritional component and are consequently suitable additional non-exhaustive examples for the second enzyme component that may be used to degrade the anti-nutritional components of the raw vegetable composition in accordance with the present invention.

Some non-exhaustive examples of endoproteases and exoproteases include Alcalase®, Neutrase® Esperase®, Protamex, Novozym® FM, Flavourzyme®, and Kojizyme®, all available from Novo Nordisk Biochem North America of Franklinton, N.C., and Enzeco® exoprotease that is available from Enzyme Development Corporation of New York, N.Y.

The enzyme-processed vegetable composition may also be further processed by freezing, hydrating, steaming, freeze-drying, canning, frying, boiling, drying, extrusion, cooking, baking, roasting, pulverizing, fermenting, enzyme, pasteurizing, extracting, milling, puffing, steam-pressure cooking, or any combination thereof after enzymatic degradation has occurred. These additional processing steps are also generally effective in deactivating any enzyme component(s) in the enzyme-processed vegetable composition. Partial degradation of anti-nutritional components in the first outer layer or the second inner layer of the vegetable composition may also occur during application of aqueous enzyme compositions that includes first and second enzyme components or the second aqueous enzyme composition.

As a first example, an enzyme-degraded raw vegetable composition that includes flatulence-causing substrates located in an inner portion of the raw vegetable composition is formed by applying a first aqueous enzyme composition that degrades the raw vegetable composition in accordance with the present invention. If a second aqueous enzyme composition that includes any enzyme component capable of degrading any flatulence-causing substrates that cause flatulence in human, such as alpha-galactosidase, beta-fructofuranosidase, beta-galactosidase, invertase, or any combination thereof, is applied to theenzyme-degraded raw vegetable composition either during or after the first aqueous enzyme composition is applied to the raw vegetable composition, degradation of flatulence-causing substrates, such as raffinose, verbascose and stachyose of the enzyme-degraded raw vegetable composition typically occurs.

Generally, the second aqueous enzyme composition is applied to the enzyme-degraded vegetable composition for a time that is sufficient for the second enzyme composition to degrade the flatulence-causing substrates, such as, for example, about 1 minute to about 12 hours. Preferably, the second aqueous enzyme composition remains in contact with the enzyme-degraded raw vegetable composition for about 5 minutes to about 120 minutes so that more than about 5 weight percent of flatulence-causing substrates are degraded in the enzyme-degraded raw vegetable composition when practicing the present invention.

As a second example, an enzyme-degraded raw vegetable composition that includes methylxanthine is formed in accordance with the present invention. As used herein, the term "methylxanthine" refers to the group of compounds used as a stimulant and diuretic typically found in vegetable compositions, such as tea, coffee, kola nuts, mate leaves, cacao bean, guarana and the like. It is understood that "methylxanthine" includes substituted forms of methylxanthine, such as, for example, caffeine. If a second aqueous enzyme composition that is capable of degrading methylxanthine, is applied to the enzyme-degraded raw vegetable composition either during or after application of a first aqueous enzyme composition is applied to the raw vegetable composition, degradation of methylxanthine in the enzyme-degraded raw vegetable composition thereby occurs to reduce the level of methylxanthine in the enzyme-degraded raw vegetable composition.

Preferably, the second aqueous enzyme composition is applied to the enzyme-degraded vegetable composition for a time that is sufficient to degrade methylxanthine, such as, for example, about 1 minute to about 8 hours. Still more preferably, the second enzyme composition that is capable of degrading methylxanthine remains in contact with the enzyme-degraded raw vegetable composition for a time that is sufficient to degrade more than about 5 weight percent methylxanthine of the raw vegetable composition when practicing the present invention. After enzymatic degradation, the enzyme-processed vegetable composition having reduced levels of methylxanthine can then be blanched to inactivate any remaining enzymes and/or further processed by pulverizing, grinding, milling, roasting, freezing, drying, freeze-drying, or any combination thereof. Subsequent additional processing by pulverizing, blending, grinding, paste-forming, roasting, freezing, drying, freeze-drying, extraction, or any combination thereof, may also deactivate the enzyme(s).

The benefits of processing vegetable compositions that include methylxanthine in accordance with the present invention include reducing the need for expensive solvent extraction equipment and chemicals that are traditionally required to decaffeinate raw vegetable compositions, such as, for example coffee bean. Additionally, the present embodiment may improve the flavor of decaffeinated coffee beans which may result in an increase in market share for a decaffeinated coffee manufacturer selling the enzyme-processed coffee beans.

As a third example, bitter flavor notes that characterize green unfermented cocoa beans may be reduced in accordance with the present invention. Cocoa beans can be divided into four categories, according to their color: fully fermented, i.e., predominantly a brown hue; purple/brown; purple; and slaty, in which slaty beans represent unfermented or green cocoa beans. Purple/brown cocoa beans include all beans showing any blue, purple or violet color on an exposed surface, whether suffused or as a patch of the cocoa beans. Purple cocoa beans should include all cocoa beans showing a completely blue, purple or violet color over the whole exposed surface.

An enzyme-degraded green unfermented cacao bean is formed in accordance with the present invention after application of an aqueous enzyme composition that includes cellulase, hemicelluase and pectinase degrades the first outer layer of green, unfermented or slaty cocoa beans. As used herein, a "green or unfermented cacao bean" includes cacao beans that do not have a sufficient quantity of amino acids and peptides required to form an acceptable cocoa flavor during subsequent roasting. Furthermore, the "green or unfermented cacao bean" include beans having less than about 40 weight percent moisture content and that have not been subjected to a fermentation step. Some non-exhaustive examples of green unfermented cacao bean that may be used in accordance with the present invention include beans derived from *Theobroma* sp., such as Ghanian cacao beans, *Amelonado* sp., *Criollo, Forastero*, or *Trinitario*.

If a second aqueous enzyme composition that includes an endoprotease, an exoprotease, or any combination thereof, is absorbed by the enzyme-degraded green, slaty or unfermented cacao bean, degradation of protein in the enzyme-degraded green unfermented cacao bean occurs. Preferably, the endoprotease, the exoprotease, or any combination thereof, is capable of degrading protein that include hydrophobic amino acids and peptides that typically contribute to the bitter flavor notes that characterize green or unfermented cacao beans. Still more preferably, the endoprotease, the exoprotease, or any combination thereof, is applied to the green or unfermented enzyme-degraded cacao bean for a time, temperature, pH and moisture content of the green unfermented enzyme-degraded cacao bean that is sufficient to degrade the bitter flavor notes in the green unfermented cacao bean.

While not wanting to be bound to theory, it is believed that the enzyme-degraded cacao bean includes sites through which the endoprotease, exoprotease, or any combination thereof, may be absorbed. Furthermore, the sites in the enzyme-degraded green unfermented cacao bean may facilitate subsequent natural fermentation of the green unfermented cacao bean by enhancing the capability of indigenous microflora of the natural fermentation process to colonize and digest the green unfermented cacao bean at the sites during the fermentation process.

The benefit of processing green unfermented cacao beans in accordance with the present invention include obtaining a less bitter cacao bean after fermentation and roasting steps. A less bitter cacao bean requires little flavor modification required during manufacture of cocoa containing products.

In an example of practicing the method of reducing the flatulence-causing substrates in a raw vegetable composition, about 740 grams of water was added to about 7.5 grams of vinegar and brought up to a temperature of about 150° F. About 2.5 milliliters of Viscozyme®L, and 2.5 milliliters of Alpha-Gal™ 600L, supplied by Novo Nordisk Biochem North America Inc., of Franklinton, N.C., were added to the vinegar and water mixture to form an aqueous enzyme composition with an initial pH of about 5.0. About 250 grams of raw collard greens were added to the aqueous enzyme composition and allowed to soak for about 30 minutes. The raw collard greens were then cooked for about 30 minutes at about 200° F. After cooking, the collard greens were drained and evaluated. Little, if any, flatulence was experienced after consumption of about 100 grams of collards even after 4 hours from the time of consumption of the collard greens.

In another example of practicing the method of reducing the flatulence-causing sugars in a raw vegetable composition, about 740 grams of water was added to about 7.5 grams of vinegar and brought up to a temperature of about 119° F. to about 123° F. About 2.5 milliliters of Viscozyme®L, and 1.25 milliliters of Alpha-Gal™ 600L, supplied by Novo Nordisk Biochem North America Inc., of Franklinton, N.C., were added to the vinegar and water mixture to form an aqueous enzyme composition with an initial pH of about 5.0. About 250 grams of raw great northern beans were added to the aqueous enzyme composition and allowed to soak for about 60 minutes. The great northern beans were then blanched for about 5 minutes at about 200° F. to deactivate the enzymes. The great northern beans did not result in any observable flatulence after human consumption.

A Method of Modifying a Vegetable Composition

As noted, the enzyme-degraded raw vegetable composition of the present invention is capable of absorbing additives to form a modified vegetable composition. The method of using one or more enzymes to modify a vegetable composition has been disclosed in U.S. Pat. No. 6,033,692. More specifically, U.S. Pat. No. 6,033,692 discloses that when raw beans are processed in accordance with the present invention, the pH of the aqueous enzyme composition generally increases over time. The increase in pH of the aqueous enzyme composition represents absorption of the vinegar by the beans during application of the aqueous enzyme composition.

Some non-exhaustive examples of additives that may be used to practice the present invention include natural and/or artificial flavors; artificial colors; naturally-occurring pigments, such as, for example, chlorophyll, anthocyanin, beta-lain, betaine, carotenoid, anthoxanthins; herbs; spices; vitamins; minerals; plant extracts; essential oils; sugars such as sucrose, fructose, glucose, or maltose; preservatives; emulsifiers, such as mono-glycerides, distilled mono-glycerides, di-glycerides, distilled di-glycerides, or lecithin; or any combination of any of these. The additives may be supplied as individual components, or supplied in various prepared mixtures of two or more components, that are subsequently combined to form the optional additives. The additives may also be applied before, during or after application of the aqueous enzyme composition to the first outer layer of the raw vegetable composition.

The method of modifying a vegetable composition in accordance with the present invention is a significant improvement in the art of vegetable processing. Typically, a vegetable composition is mechanically modified, such as by peeling, grinding, pulverizing, prior to inclusion of an additive, followed by subsequent processing by conventional means. The added step of mechanical modification, along with any safety and health hazards that accompany using equipment involved in the mechanical modification of vegetables, may be eliminated when practicing the present invention. Additionally, the present invention accomplishes in situ modification of a raw vegetable composition.

As an example of the present embodiment that modifies raw vegetable composition, about 740 grams of water was added to about 7.5 milliliters of vinegar and brought up to a temperature of about 119° F. to about 123° F. About 2.5 milliliters of Viscozyme®L, supplied by Novo Nordisk Biochem North America Inc., of Franklinton, N.C., was added to the vinegar and water mixture to form an aqueous enzyme composition with an initial pH of about 4.8. About 250 grams of raw pinto beans were added to the aqueous enzyme composition and allowed to soak for about 60 minutes. The change in pH, indicating the absorption of vinegar is presented in Table 4 below:

TABLE 4

| TIME (minute) | TEMPERATURE (° F.) | pH |
| --- | --- | --- |
| 0 | 123.1 | 4.78 |
| 15 | 118.5 | 5.11 |
| 30 | 117.7 | 5.38 |
| 45 | 118.9 | 5.56 |
| 60 | 119.2 | 5.70 |

Property Determination and Characterization Techniques

Various analytical techniques are employed herein. An explanation of these techniques follows. All values presented in this document for a particular parameter, such as moisture content, are based on the "as is" sample and are therefore on a "wet basis", unless otherwise specified herein.

To determine the weight percent hydration, in a particular sample, the sample is accurately weighed prior to application of the aqueous enzyme composition. The final weight of the enzyme-degraded sample and/or the enzyme-processed sample is then accurately determined after application of the aqueous enzyme composition. The weight percent hydration in the sample, is then calculated by subtracting the initial weight of the sample from the weight of enzyme-degraded or enzyme-processed sample. The difference is divided by the final weight of the enzyme-degraded sample and/or the enzyme-processed sample and multiplied by 100. The formula is written below:

$$\frac{Weight_{final} - Weight_{initial}}{Weight_{final}}$$

To determine the absorbency of water in a particular sample, the sample is accurately weighed prior to application of the aqueous enzyme composition. The final weight of the hydrated sample is then accurately determined after application of water to the vegetable composition. The absorbency of water in the sample, is calculated by subtracting the initial weight of the sample from the weight of the hydrated vegetable composition. The difference, expressed in grams of water absorbed by the vegetable composition, is divided by the amount of time that the water is applied to the vegetable composition.

To determine the specific absorbency, the absorbency of the vegetable composition is divided by the initial weight of the sample.

CONCLUSION

In view of the foregoing disclosure and embodiments, it is believed that processing a raw vegetable composition in accordance with the present invention represents a significant improvement in the art of vegetable processing. The development of an effective process that reduces the complexity and costs associated with vegetable production, by reducing the first outer layer of a vegetable composition that typically hinders processing, creates a vegetable product with enhanced processing characteristics. Furthermore, the development of an in situ method of processing and modifying a raw vegetable composition greatly enhances the ability of a food manufacturer to produce vegetable products that offer a wide variety of nutritional characteristics to consumers.

Although the present invention has been described with reference to preferred embodiments, workers skilled in the art will recognize that changes may be made in form and detail without departing from the spirit and scope of the invention.

The invention claimed is:

1. A method of enzymatically degrading a raw vegetable composition prior to human consumption, the method comprising:
   providing a raw whole vegetable composition having a moisture content of less than about 30 weight percent;
   applying an aqueous enzyme composition comprising water, a protease and a cellulase to the raw vegetable composition under normal atmospheric pressures for a time that is sufficient to degrade the raw vegetable composition, wherein the aqueous enzyme composition is at an initial pH of between about 2.0 and 7.0; and
   deactivating the aqueous enzyme composition.

2. The method of claim 1 wherein the aqueous enzyme composition is effective to degrade a first outer layer of the raw vegetable composition.

3. The method of claim 1 wherein the aqueous enzyme composition is effective to reduce the cook time of the raw vegetable composition.

4. The method of claim 1 wherein the aqueous enzyme composition is effective to hydrate the raw vegetable composition.

5. The method of claim 4 wherein the raw vegetable composition absorbs more than about 0.003 grams water per minute per gram of the raw vegetable composition.

6. The method of claim 1 and further including applying a second aqueous enzyme composition to the raw vegetable composition, wherein the second aqueous enzyme composition comprises at least one enzyme that is selected from the group consisting of alpha-galactosidase, mannanase, beta-gluconase, beta-gluconase, arabinase, xylanase, beta-galactosidase, invertase, beta-fructotijranosidase, alpha-amylase, beta-amylase, pectinase, pectin depolymerase, pectin methyl esterase, pectin lyase, glucoamylase, oligo-1,6 glucosidase, protease, lactase, beta-d-glucosidase, and any combination thereof.

7. The method of claim 1 wherein deactivating the enzyme composition includes freezing, drying, freeze-drying, canning, flying, hydrating, boiling, extruding, steaming, blanching, blending, cooking, baking, roasting, fermenting, peeling, pasteurizing, extracting, grilling, milling, puffing, microwaving, enzymatic degradation, grinding, grating, pulverizing, steam-pressure cooking, or any combination of any of these.

8. A method of enzymatically processing a vegetable composition prior to human consumption, the method comprising:
   providing a raw whole vegetable composition having a moisture content of less than about 30 weight percent;
   applying a first enzyme composition comprising water, at least one protease and a cellulase to the raw vegetable composition under normal atmospheric pressures for a time that is sufficient to form an enzyme-degraded raw vegetable composition, wherein the first enzyme composition is at a pH of between about 2.0 and 7.0;

applying a second enzyme composition comprising water and a carbohydrase to the enzyme-degraded raw vegetable composition; and deactivating the first enzyme composition and the second enzyme composition.

9. The method of claim 8 wherein the second enzyme composition comprises at least one enzyme that is selected from the group consisting of hemicellulase, alpha-galactosidase, mannanase, beta-gluconase, beta-gluconase, arabinase, xylanase, beta-galactosidase, invertase, beta-fructofuranosidase, alpha-amylase, beta-amylase, pectinase, pectin depolymerase, pectin methyl esterase, pectin lyase, glucoamylase, oligo-1,6 glucosidase, lactase, beta-d-glucosidase, and any combination thereof.

10. A method of processing a vegetable composition prior to consumption, the method comprising:

providing a raw whole vegetable composition having a moisture content of less than about 40 weight percent;

applying an enzyme composition having a pH of between about 2.0 and 7.0 to the raw vegetable composition under normal atmospheric pressures for a time that is sufficient to degrade the raw vegetable composition, wherein the enzyme composition includes water, a first enzyme component, and a second enzyme component, wherein the first enzyme component includes a cellulase that degrades the raw vegetable composition, and wherein the second enzyme component includes a protease that degrades a protein or a peptide; and deactivating the enzyme composition.

11. The method of claim 10 wherein the raw vegetable in said composition is a legume, a soybean, an edible seed, a green unfermented cocoa bean, or any combination of any of these.

12. The method of claim 10 wherein the protease degrades a hydrophobic amino acid containing protein, a hydrophobic amino acid-containing peptide, or any combination of any of these.

13. A method of processing a vegetable composition prior to consumption, the method comprising:

providing a raw whole bean having a moisture content of less than about 30 weight percent; and applying an enzyme composition having a pH of between about 2.0 and 7.0 to the raw bean under normal atmospheric pressures for a time that is sufficient to degrade the raw bean, wherein the enzyme composition includes water, at least one protease, and a cellulase that degrades the raw whole bean.

14. A method of processing a vegetable composition prior to consumption, the method comprising:

providing a raw whole vegetable composition having a moisture content of less than about 40 weight percent;

applying an enzyme composition having an initial pH of between about 2.0 and 7.0 to the raw vegetable composition for a time that is sufficient to degrade the raw vegetable composition, wherein the enzyme composition includes water, at least one cellulase, at least one protease, alpha-galactosidase and alpha-amylase, wherein the enzyme composition is effective to degrade the raw vegetable composition; and deactivating the enzyme composition.

15. The method of claim 14 wherein the raw vegetable composition is a legume, a soybean, a grain, an edible seed, a green unfermented cocoa bean, or any combination of any of these.

16. The method of claim 14 wherein the enzyme composition is effective to degrade raffinose and stachyose in the raw whole vegetable composition.

\* \* \* \* \*